United States Patent
Duggins (10) Patent No.: US 10,857,381 B2
(45) Date of Patent: Dec. 8, 2020

(54) INTEGRATED PHOTOTHERAPY APPARATUS AND METHODS

(71) Applicant: LOMA LINDA UNIVERSITY, Loma Linda, CA (US)

(72) Inventor: Janel A. Duggins, Murrieta, CA (US)

(73) Assignee: LOMA LINDA UNIVERSITY, Loma Linda, CA (US)

( * ) Notice: Subject to any disclaimer, the term of this patent is extended or adjusted under 35 U.S.C. 154(b) by 0 days.

(21) Appl. No.: 15/965,781

(22) Filed: Apr. 27, 2018

(65) Prior Publication Data

US 2018/0243583 A1    Aug. 30, 2018

Related U.S. Application Data

(63) Continuation-in-part of application No. PCT/US2016/059559, filed on Oct. 28, 2016.

(60) Provisional application No. 62/248,173, filed on Oct. 29, 2015.

(51) Int. Cl.
| | |
|---|---|
| A61N 5/06 | (2006.01) |
| A61B 5/00 | (2006.01) |
| G16H 40/63 | (2018.01) |
| A61B 5/145 | (2006.01) |
| A61G 11/00 | (2006.01) |

(52) U.S. Cl.
CPC .............. *A61N 5/0621* (2013.01); *A61B 5/00* (2013.01); *A61B 5/002* (2013.01); *A61B 5/14546* (2013.01); *A61B 5/443* (2013.01); *A61B 5/4836* (2013.01); *A61B 5/6833* (2013.01); *A61B 5/742* (2013.01); *A61B 5/7475* (2013.01); *A61N 5/06* (2013.01); *G16H 40/63* (2018.01); *A61B 2503/04* (2013.01); *A61B 2562/0271* (2013.01); *A61B 2562/185* (2013.01); *A61G 11/00* (2013.01); *A61N 2005/0628* (2013.01)

(58) Field of Classification Search
CPC ............................. A61N 5/0621; G16H 40/63
USPC ......................................................... 607/88
See application file for complete search history.

(56) References Cited

U.S. PATENT DOCUMENTS

2006/0206173 A1* 9/2006 Gertner ................ A61N 5/0616
607/88

* cited by examiner

*Primary Examiner* — Nadia A Mahmood
(74) *Attorney, Agent, or Firm* — Womble Bond Dickinson (US) LLP (57) ABSTRACT

Embodiments of systems and methods for an integrated phototherapy system that can include integrating a bili light, radiometer, and transcutaneous bilirubin sensor are disclosed. In some embodiments, the integrated phototherapy system has a control system that can receive and send data and automate features of the phototherapy system. Data that can be input by a healthcare provider and/or measured by the system can include treatment time, distance between the patient and the bili light, intensity level, irradiance level, bilirubin level, temperature, and the light intensity or irradiance of other light sources or pieces of equipment. The phototherapy system can be compatible with any electronic healthcare records system, and measured data can aggregated and uploaded to such a system.

24 Claims, 6 Drawing Sheets

INTEGRATED PHOTOTHERAPY APPARATUS AND METHODS

CROSS REFERENCE TO RELATED APPLICATIONS

This application is a continuation-in-part of, and claims priority to and the benefit of, PCT Patent Appln. No. PCT/US2016/059559, filed Oct. 28, 2016, which claims priority to U.S. Provisional Application Ser. No. 62/248,173, filed Oct. 29, 2015.

BACKGROUND

Field of Invention

This disclosure relates generally to phototherapy and, more particularly, to systems, devices, and methods for administering phototherapy with a light source, radiometer, and a transcutaneous bilirubin reader.

Description of Related Art

Phototherapy is a method of treating various ailments with exposure to light. Efficacy of treatment depends on a variety of factors, including, for example, the wavelength of light used, the distance between the patient and the light source, the amount of time the patient is exposed to the light, and the irradiance of the light. Phototherapy can be used to treat physical ailments, such as skin conditions, mental and psychological conditions, or physiological conditions, such as hyperbilirubinemia.

SUMMARY

Embodiments of systems and methods for an integrated phototherapy system are disclosed. For example, an embodiment of such a system can include integrating a bili light, radiometer, and transcutaneous bilirubin reader in a manner that allows greater and more efficient care capabilities for providing care to patients. In some embodiments, the integrated phototherapy system has a control system that can receive and send data and automate features of the phototherapy system. Data that can be input by a healthcare provider and/or measured by the system, for example, can include treatment time, distance between the patient and the bili light, intensity level, desired or optimum irradiance level, a total up time for the light source (i.e., the total amount of time the light or lights have been in use, and/or bilirubin level. As described herein, automated features, for example, can include an automatic shutoff feature, automatic sensing and notification of patient or bili light position, and/or automatic adjustment of bili light intensity.

In some embodiments, administration of phototherapy to an infant with jaundice includes exposing the infant to blue light (e.g., light having substantial spectral power between 420 nm and 470 nm) from a bili light that has one or more than one overhead light and/or one or more than one light embedded in a blanket. In embodiments, the wavelength does not necessarily have to be in the 420 nm to 470 nm range. Other wavelengths, which will correspond to other colors, can be used according to various embodiments. Other light sources can be used in various embodiments.

For example, one or more lights can be embedded in a mat on which the infant can lie. In embodiments, lights from multiple sources can be used. For example, a mat can be used and a blanket with one or more embedded lights can be placed over the infant or an overhead light can be placed to direct light at the infant. In certain embodiments, a phototherapy system for treatment of newborn jaundice includes a bili light, radiometer, and a transcutaneous bilirubin reader. A radiometer is an instrument used to measure the irradiance of the light received by a patient. When a patient is underneath phototherapy lights, the radiometer is placed at the patient's level where he/she is receiving the most light to ensure that the light irradiance that is needed for treatment is actually reaching the patient.

In current phototherapy systems, the light source, radiometer, and transcutaneous bilirubin reader are separate pieces of equipment with each having only one function. This separation of the pieces of equipment creates a number of challenges and limitations, including increased risk of infections, increased risk of workplace hazards and accidents, decreased efficiency of hospital staff, increased length of treatment times, longer hospital stays, and increased costs for hospitals and patients' families.

For example, there is often less than one radiometer per phototherapy patient, necessitating the sharing of one piece of equipment among multiple patients. In some instances, one radiometer may be shared among over 80 NICU patients. Likewise, most facilities have only one transcutaneous bilirubin reader, which also requires sharing. Sharing equipment with multiple patients, especially infants, increases the risk of transporting germs. Even though the equipment is cleaned after each use, there is still the chance of human error.

Also, obtaining a shared radiometer can decrease efficiency and productivity of hospital staff and increase the risk of workplace hazards. In some instances, the radiometer is kept in a locked cabinet that requires the entry of a username and password to open the cabinet, and requires logging the radiometer out under a patient's name. This process can be very time consuming. Further, the American Academy of Pediatrics imposes strict guidelines on the light irradiance a patient should receive to achieve optimal therapy, and nurses are required to check and document the light intensity reading twice a day.

When multiple patients are receiving phototherapy, for example, nurses can experience difficulties and expend much time searching for and obtaining radiometers in the limited time they have in their busy days. In some instances, the nurse has few opportunities to carefully leave the bedside of his/her patients to obtain the radiometer, and if the radiometer is being used for other patients, then the nurse will have to delay and expend much time in obtaining the radiometer. These efforts decrease nurses' productivity, decreases the time nurses' are able to spend with their patients, and increase the risks for workplace hazards and accidents.

Further, having a separate radiometer, transcutaneous bilirubin reader, and phototherapy light may also prolong patient treatment times and, consequently, hospital stays and hospital and patient costs. When a radiometer cannot be readily accessed for a patient, the patient may fail to achieve optimal therapy for a period of up to a day. For example, if nurses work twelve-hour shifts and one nurse is able to check the light intensity/irradiance early in his/her shift, but the following nurse is not able to check the light intensity/irradiance until the end of his/her shift, then the patient's light irradiance levels remain unmonitored for the vast majority of a day. For that amount of time the light intensity/irradiance is unknown and may not be achieving optimal therapy. The more time the patient receives sub-optimal therapy, the longer time the patient spends under the phototherapy lights.

In embodiments described herein, the light source, radiometer, and bilirubin reader are integrated with the phototherapy apparatus.

In one embodiment, a method for administering phototherapy to treat newborn jaundice in a patient using a phototherapy system comprises: positioning the patient to receive phototherapy from a bili light, which can include an overhead light source, blanket, mat, or any other light source; determining an initial distance between the patient and the bili light; determining a desired level of bilirubin in the patient; inputting the initial distance and the desired level of bilirubin into a user interface of the phototherapy system; delivering phototherapy light to a patient; and measuring irradiance with a radiometer, the radiometer being integrated with the phototherapy apparatus. The phototherapy light can be set to delivery phototherapy at a desired initial range, for instance 30 to 50 microwatts, or any other range selected by the user. The user can also set a floor or ceiling for irradiance. For example, the user can set a floor of 30 microwatts so that irradiance never falls below that amount. A notification can be generated if irradiance does fall below that amount or feedback to the light source can automatically adjust the light to increase irradiance. Likewise, a ceiling can be set such that by the same principle the light is automatically dimmed or a notification is generated if too high an irradiance is detected. As described in more detail below, a potentiometer can be used to increase or decrease irradiance, automatically or responsive to user input.

In one feature, a transcutaneous bilirubin sensor is attached to the patient. The transcutaneous bilirubin sensor is integrated with the phototherapy apparatus as well. The sensor can be used to monitor the bilirubin level of the patient before, during, and/or after phototherapy treatment. The transcutaneous bilirubin sensor can be set to continuously or intermittently provide readings. For example, the sensor can be set to provide data every hour, two hours, or any other time increment selected by a user. This data can be displayed in a number of ways. For example, it can be automatically uploaded and displayed with the patient's electronic healthcare records. This way, the data can be monitored from a separate computing device. The bilirubin reader can also send data to the radiometer, where it can be displayed on the radiometer's display. In embodiments, data from the transcutaneous bilirubin reader can be displayed on a display of the light source. In embodiments, the transcutaneous bilirubin sensor can further include a temperature sensor to provide the patient's temperature. In embodiments, the transcutaneous bilirubin sensor can further provide an indication of the distance between the patient and the light source.

In another feature, a therapy completed signal or notification is received from the user interface; and, if the phototherapy system has an automatic shutoff option enabled, the bili light is confirmed to be off, otherwise, the bili light is shut off.

In another feature, a check distance signal is received from the user interface; a second distance between the patient and the bili light is determined; the initial distance is compared to the second distance; and, if the second distance is greater than the first distance, the patient or the bili light is repositioned so that the patient and the bili light are closer together, otherwise, the patient or the bili light is repositioned so that the patient and the bili light are farther apart.

In another feature, a low irradiance signal is received from the user interface; and a potentiometer is adjusted to increase intensity of the bili light.

In another feature, a low irradiance signal is received from the user interface, for example based on the preset value input by the user; and the patient or the bili light is repositioned so that the patient and the bili light are closer together. In another embodiment, a computer-implemented method for administering phototherapy to treat newborn jaundice in a patient using a phototherapy system comprises: generating an interactive user interface; receiving a shutoff input relating to an automatic shutoff option via the interactive user interface, wherein the shutoff input is either an on input or an off input; receiving a desired level of irradiance for the patient via the interactive user interface; turning on a bili light via a bili light controller; and receiving a measured irradiance level from a radiometer, the radiometer being integrated with the phototherapy system, and the transcutaneous bilirubin reader being integrated with the phototherapy system as well. Data from the bilirubin reader can further be displayed via the interactive user interface.

In one feature, a desired level of bilirubin in the patient is received via the interactive user interface; a measured bilirubin level is received from a transcutaneous bilirubin sensor; the measured bilirubin level is compared to the desired bilirubin level; and if the measured bilirubin level is less than or equal to the desired bilirubin level: a therapy completed signal is generated, and if the shutoff input is an on input, the bili light is shut off.

In another feature, an initial distance between the patient and the bili light is received via the interactive user interface; an intensity of the bili light is received from the bili light controller; a second distance between the patient and the bili light is calculated, based at least in part on the intensity of the bili light and the measured irradiance level; and if the calculated second distance is different from the initial distance, a check distance signal is generated. In another feature, a potentiometer is adjusted via a potentiometer controller to increase the intensity of the bili light if the second distance is greater than the initial distance; otherwise, a potentiometer is adjusted via a potentiometer controller to decrease the intensity of the bili light. This adjustment process can be fully automated via the feedback provided from the radiometer and the bilirubin reader, or this process can be manual and fully controlled by a user. In embodiments, the automated process can be overwritten by a user.

In another feature, the measured irradiance level is compared to the desired irradiance level, and if the measured irradiance level is different from the desired irradiance level, a check light signal is generated. In another feature, a potentiometer is adjusted via a potentiometer controller to increase the intensity of the bili light if the measured irradiance level is less than the desired irradiance level; otherwise, a potentiometer is adjusted via a potentiometer controller to decrease the intensity of the bili light.

In another embodiment, a phototherapy apparatus comprises: a bili light integrated with the apparatus, wherein the bili light is configured to deliver phototherapy to a patient; a radiometer integrated with the apparatus, wherein the radiometer is configured to measure irradiance; a controller electrically connected to the bili light and to the radiometer, wherein the controller is configured to: receive measured irradiance values from the radiometer, receive an intensity level setting from the bili light, send signals to the bili light to turn on the bili light, and send signals to the bili light to shut off the bili light. The controller can further be configured to receive values indicating bilirubin levels form a transcutaneous bilirubin reader, which is also integrated with the phototherapy apparatus. This can further result in sending signals to the bili light to increase or decrease intensity levels or start and stop phototherapy altogether. In embodiments, the transcutaneous bilirubin sensor that is placed on the patient's skin can wirelessly communicate with other aspects of the phototherapy system. For example, a transcutaneous bilirubin sensor patch on the patient's skin can send bilirubin levels to the light source or radiometer for display on their respective display screens.

In one feature, the radiometer is integrated with the phototherapy apparatus via a fixed connection. In another feature, the radiometer is integrated with the phototherapy apparatus via an extendible cord. In another feature, the radiometer is integrated with the phototherapy apparatus via a wireless communication path or via any other communications means, such as Bluetooth, USB, or other electrical or electromechanical connectors.

In another feature, a potentiometer is integrated with the apparatus, wherein the potentiometer is configured to adjust the intensity level setting of the bili light; and the controller is further electrically connected to the potentiometer and configured to send signals to the potentiometer to adjust the intensity level setting of the bili light. As noted, the potentiometer can be configured to automatically adjust intensity levels based on feedback from the radiometer and/or the transcutaneous bilirubin reader.

In another feature, a digital display is configured to display the measured light irradiance, and display a time period that the bili light has been in operation. For example, the total treatment time for a specific patient can be displayed, as well as the total time the phototherapy system itself has been and used. The digital display can further display the current date and time, when therapy was started and stopped, patient temperature, bilirubin levels from the bilirubin sensor, all input settings e.g. irradiance values or range of values, intensity readings, and additional data. Total therapy time can also be calculated, for example by noting the start of therapy and keeping track of total off times, which can then be subtracted from the time elapsed since the start of therapy.

In another feature, a first logical memory address is configured to store a target irradiance level; a second logical memory address is configured to store a measured irradiance value; and the controller is further configured to send a check light signal when the measured irradiance value drops below the target irradiance level.

In another feature, a bilirubin sensor is integrated with the apparatus, wherein the bilirubin sensor is configured to measure bilirubin level of the patient. In another feature, a first logical memory address is configured to store a target bilirubin level; a second logical memory address is configured to store a measured bilirubin level; and the controller is further configured to send a therapy complete signal when the measured bilirubin level is less than or equal to the target bilirubin level. In another feature, the therapy complete signal is sent to the bili light and shuts off the bili light.

In another feature, a first logical memory address is configured to store an initial distance between the patient and the bili light; a second logical memory address is configured to store the intensity level setting of the bili light; a third logical memory address is configured to store a measured irradiance value; and the controller is further configured to calculate a second distance between the patient and the bili light based at least in part on the intensity level setting of the bili light and the measured irradiance value, and to send a check distance signal if the calculated second distance is different from the initial distance.

In another feature, a timer is configured to record an elapsed phototherapy time period. In embodiments, the initial start time can be logged, and the timer can keep track of every time phototherapy is stopped. The total time off can be subtracted from the time since therapy initially began to provide an overall total of actual therapy time. In another feature, a memory is configured to store a target phototherapy time period; and the controller is further configured to send a time complete signal when the elapsed phototherapy time period reaches the target phototherapy time period. In another feature, the time complete signal is sent to the bili light and shuts off the bili light, if the automated shutoff option is enabled. In embodiments, a notification can be sent and a user can manually shut off the bili light if desired. In embodiments, a combination of automated and manual control can be provided, for the shutoff feature or any other feature. For example, an automated shutoff can be initiated, but this can be overwritten manually by a user.

BRIEF DESCRIPTION OF THE DRAWINGS

Some embodiments are depicted in the accompanying drawings for illustrative purposes, and should in no way be interpreted as limiting the scope of the inventions described herein. In addition, various features of different disclosed embodiments can be combined to form additional embodiments, which are part of this disclosure. Any feature or structure can be removed or omitted. Throughout the drawings, reference numbers may be reused to indicate correspondence between reference elements.

DETAILED DESCRIPTION

Although certain embodiments and examples are disclosed herein, inventive subject matter extends beyond the examples in the specifically disclosed embodiments to other alternative embodiments and/or uses, and to modifications and equivalents thereof. Thus, the scope of the claims appended hereto is not limited by any of the particular embodiments described below. For example, in any method or process disclosed herein, the acts or operations of the method or process may be performed in any suitable sequence and are not necessarily limited to any particular disclosed sequence. Various operations may be described as multiple discrete operations in turn, in a manner that may be helpful in understanding certain embodiments; however, the order of description should not be construed to imply that these operations are order dependent, unless specifically stated. Additionally, the structures, systems, and/or devices described herein may be embodied as integrated components or as separate components, if not specifically defined in a certain manner. For purposes of comparing various embodiments, certain aspects and advantages of these embodiments are described. Not necessarily all such aspects or advantages are achieved by any particular embodiment. Thus, for example, various embodiments may be carried out in a manner that achieves or optimizes one advantage or group of advantages as taught herein without necessarily achieving other aspects or advantages as may also be taught or suggested herein.

Figure 1:
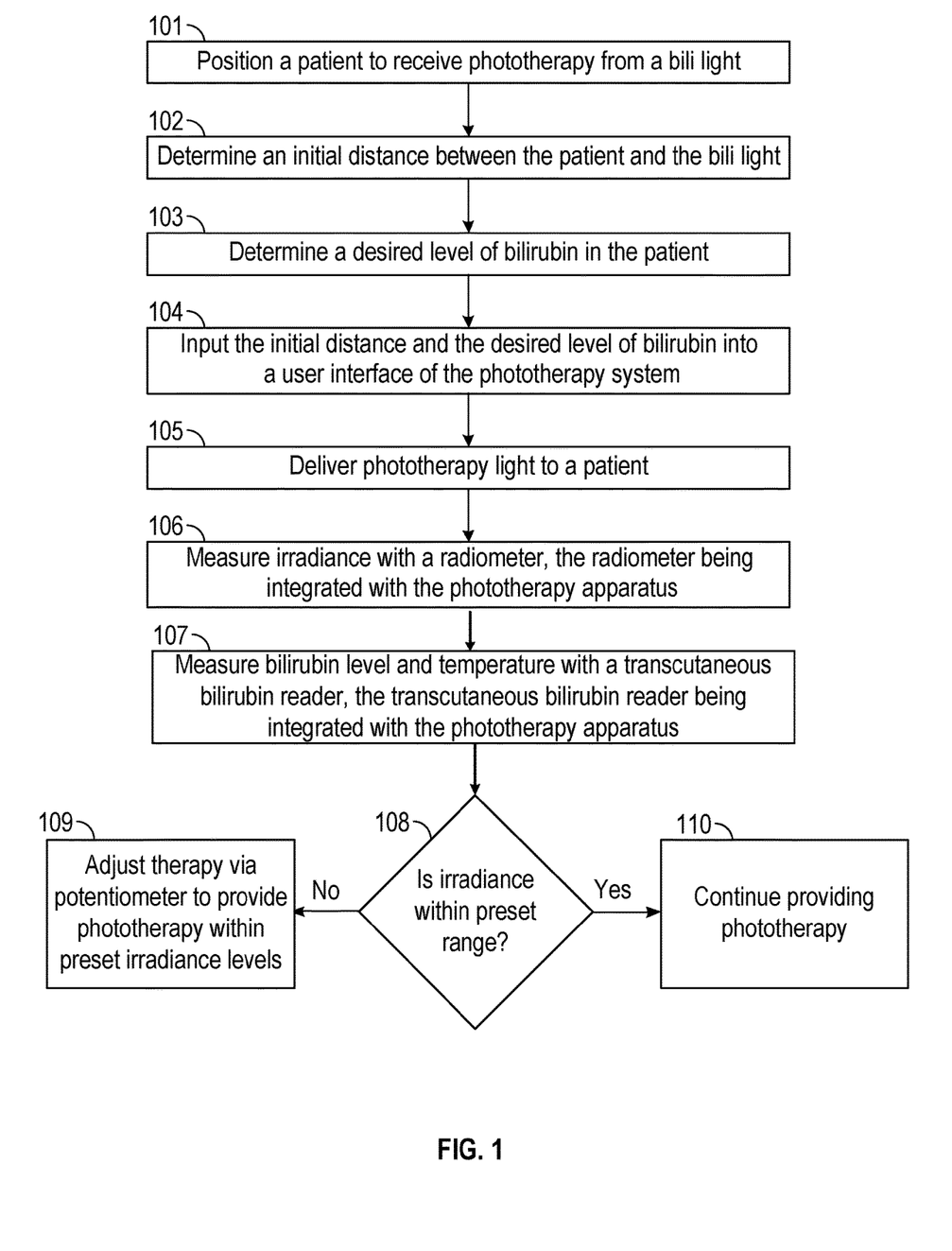
FIG. 1 is a flow chart illustrating a method for administering phototherapy according to embodiments.
Figure 6:
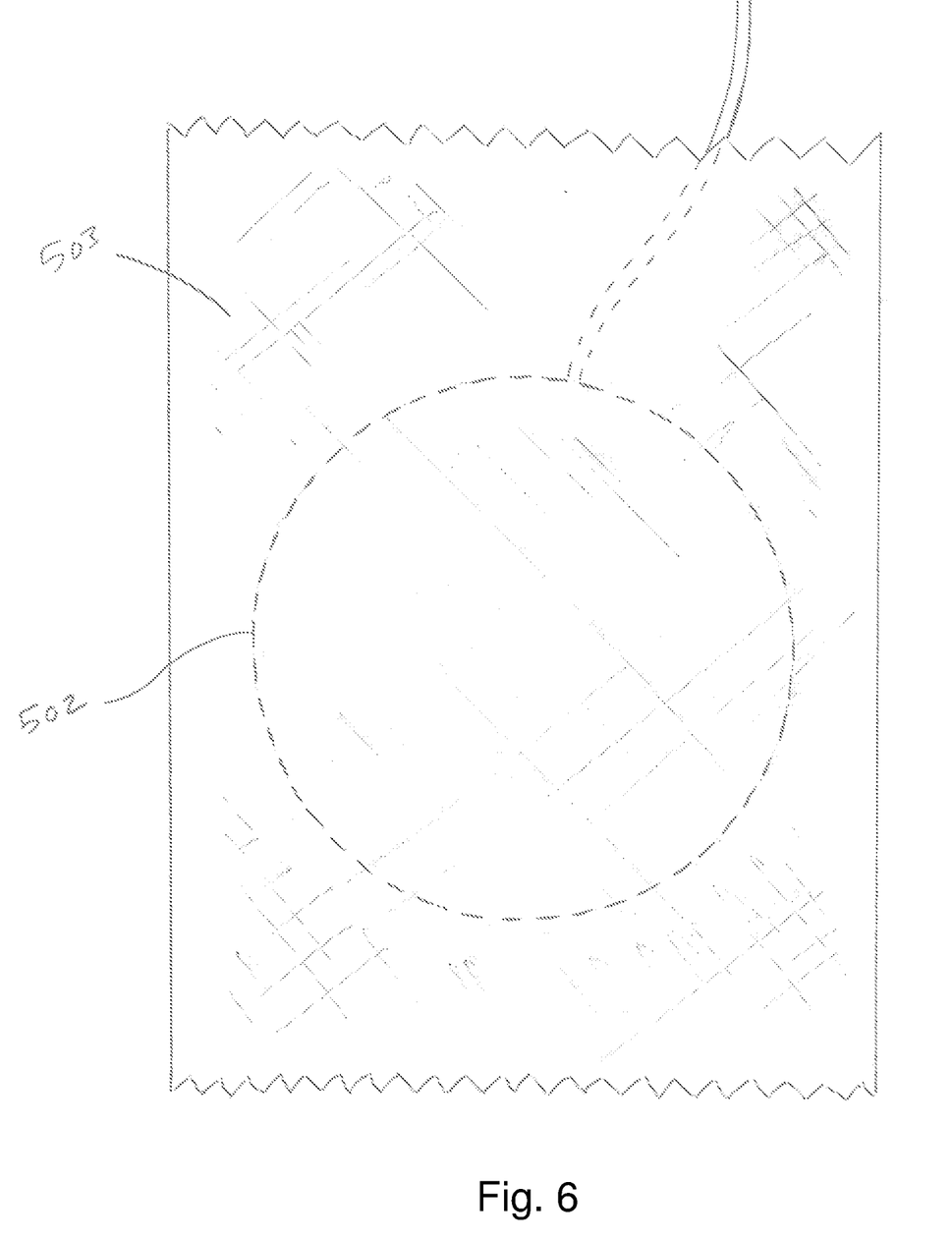
FIG. 6 is a representation of a sensor or a transcutaneous bilirubin reader, including a substantially opaque covering, according to certain embodiment of the present technology.

FIG. 1 is a flow chart illustrating a method a method for administering phototherapy to treat newborn jaundice in a patient using a phototherapy system. In step 101, a patient is positioned to receive phototherapy from a bili light. In step 102, an initial distance between the patient and the bili light is determined. In step 103, a desired level of bilirubin in the patient is determined. In step 104, the initial distance and the desired level of bilirubin are input into a user interface of the phototherapy system. In step 105, phototherapy light is delivered to a patient. In step 106, irradiance is measured with a radiometer, where the radiometer is integrated with the phototherapy apparatus. That is, the radiometer can be physically placed within a dock in the phototherapy apparatus, as described more thoroughly with respect to FIG. 6 below. In step 107, bilirubin level and temperature can be measured with a transcutaneous bilirubin reader/sensor, the transcutaneous bilirubin reader being integrated with the phototherapy system. At step 108, a determination can be made if irradiance is within a preset range. If so, phototherapy can continue being provided 110 according to the current settings. If not, phototherapy can be adjusted, automatically in certain embodiments, via a potentiometer to provide phototherapy within preset irradiance levels 109.

Figure 2:
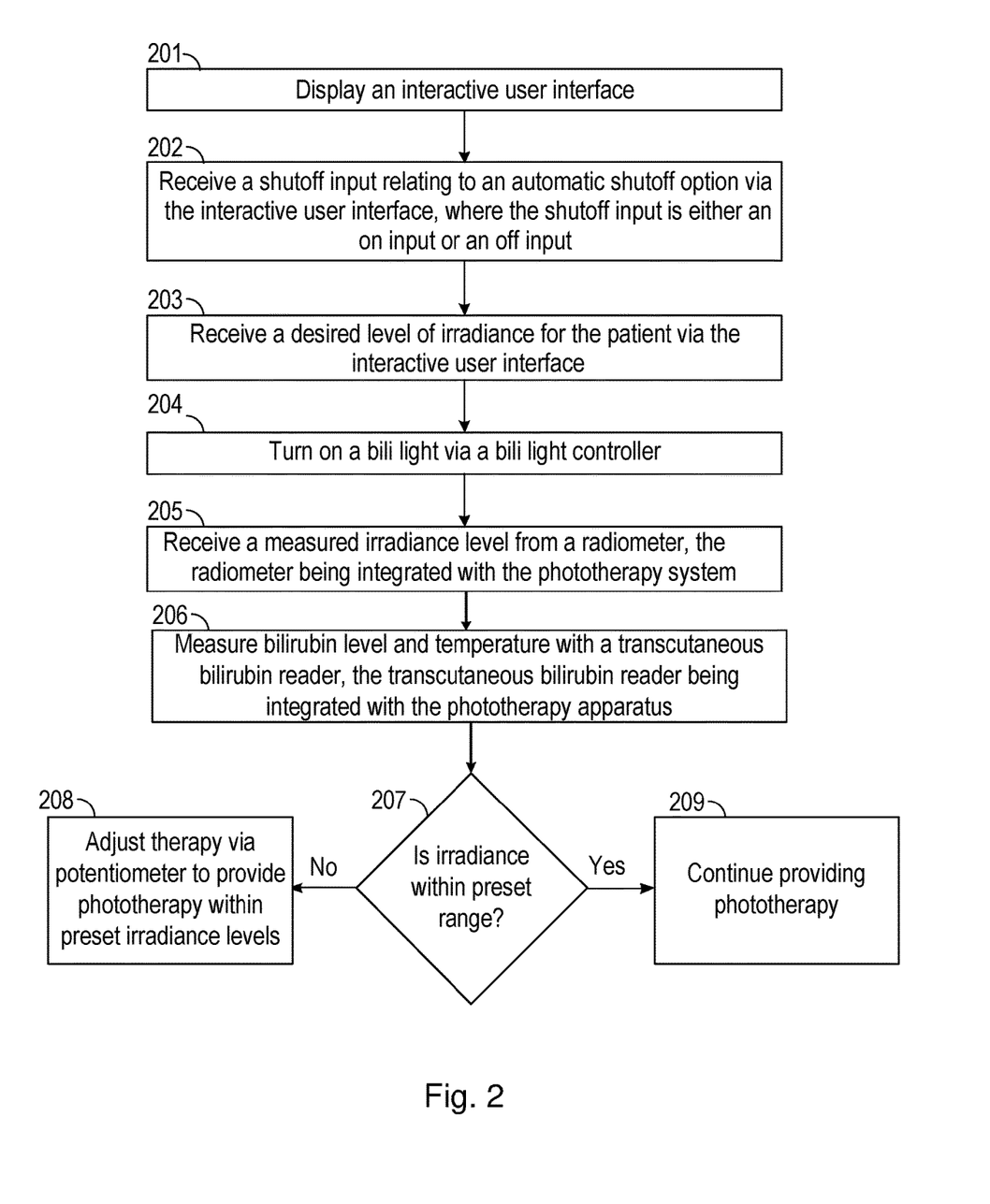
FIG. 2 is a flow chart illustrating a method for administering phototherapy according to embodiments.

FIG. 2 is a flow chart illustrating a computer-implemented method for administering phototherapy to treat newborn jaundice in a patient using a phototherapy system. In step 201, an interactive user interface is displayed on, e.g., a display screen associated with the phototherapy system. In some embodiments, the display screen comprises a display that is integrated with the phototherapy system. That is, the display can be integrated with the light source, but the same data can be displayed or mirrored at separate computing devices or stations. In certain embodiments, the display screen is a mobile device display, wherein the mobile device is carried by a nurse, physician, or other healthcare provider. In step 202, a shutoff input relating to an automatic shutoff option is received via the interactive user interface. The shutoff input can be either an on input or an off input. In step 203, a desired level of irradiance for the patient is received via the interactive user interface. In step 204, a bili light is turned on via a bili light controller. In step 205, a measured irradiance level is received from a radiometer, the radiometer being integrated with the phototherapy system. In step 206, bilirubin level and temperature can be measured with a transcutaneous bilirubin reader/sensor, the transcutaneous bilirubin reader being integrated with the phototherapy system. At step 207, a determination can be made if irradiance is within a preset range. If so, phototherapy can continue being provided 209 according to the current settings. If not, phototherapy can be adjusted, automatically in certain embodiments, via a potentiometer to provide phototherapy within preset irradiance levels 208.

Figure 3:
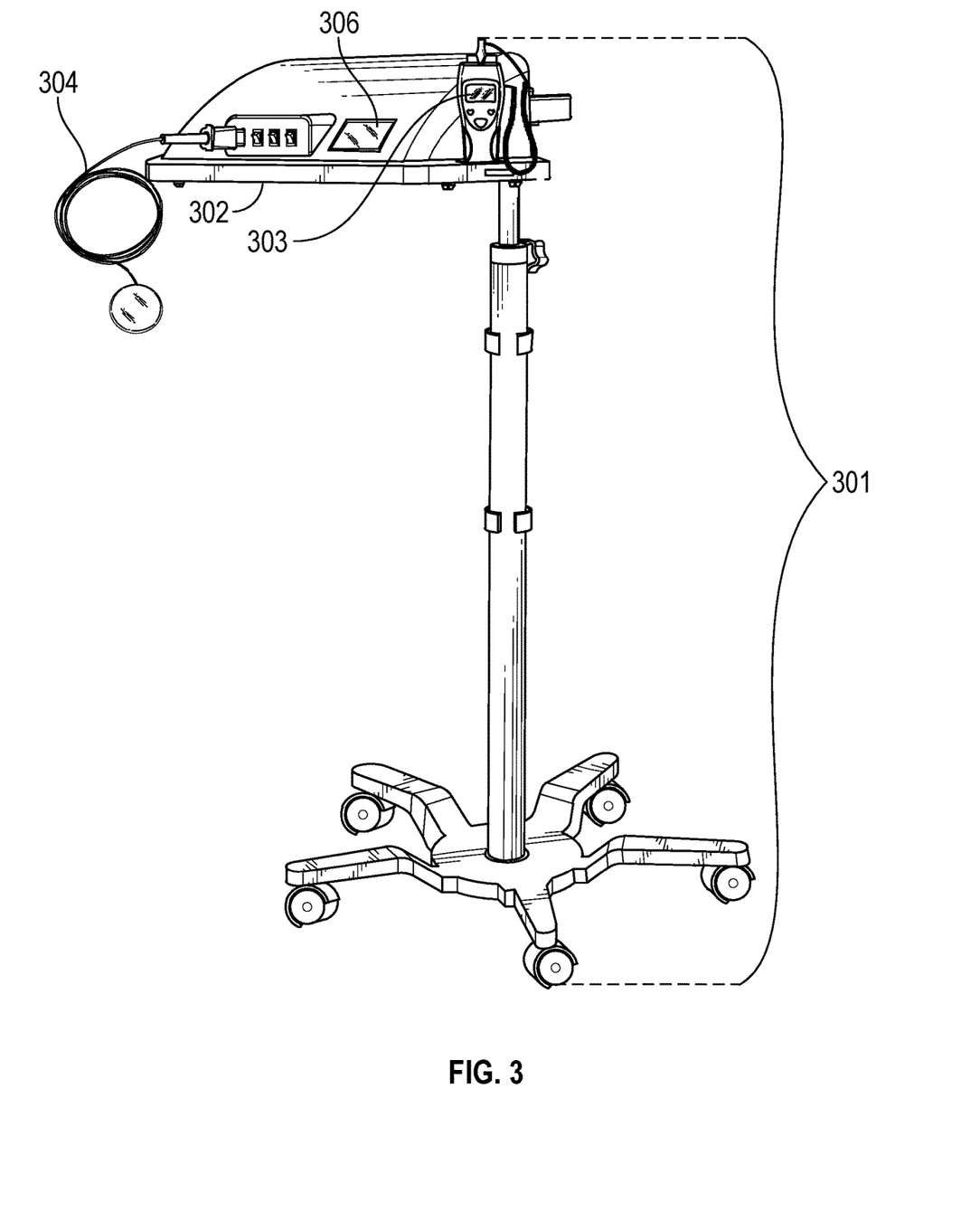
FIG. 3 is a representation of an integrated phototherapy apparatus according to embodiments.

FIG. 3 is a representation of an integrated phototherapy apparatus. The light source 302 is integrated with the phototherapy apparatus 301, and the radiometer 303 is integrated with the phototherapy apparatus. The transcutaneous bilirubin reader 304 can further be integrated with the phototherapy apparatus 301. In some embodiments the light source is overhead of the patient. In embodiments, the phototherapy apparatus can include a dedicated display 306.

In some embodiments the light source is in a blanket. The light source can have the capability of delivering single, double, or triple phototherapy. For example, in embodiments, the light source can be an overhead light that includes multiple sets of lights, wherein each set itself includes one or more lights. Thus, in embodiments, the light source can include a tray of three sets of lights, and phototherapy settings can include the optional use of one, two, or all three sets of lights, which respectively can be denoted as single, double, and triple phototherapy. The light source can also have the capability of delivering different light spectrum wavelengths and/or ranges of wavelengths. In some embodiments the light source is one or more light emitting diodes. Although the radiometer and transcutaneous bilirubin reader are integrated with the phototherapy apparatus, in embodiments the radiometer and transcutaneous bilirubin reader can be used with other light sources that do not have their own associated integrated equipment. For example, a radiometer or bilirubin sensor can be used to provide data from a patient that is exposed to light from a standalone light source. A toggle switch, program buttons, a scannable code, or other means can be used to indicate to the control unit that the bilirubin reader and radiometer are providing data from a second light source, which could even be associated with a separate patient. The user will be able to specify that the second light source is being provided and that, for example, the readings are coming from a different light source and/or patient.

Figure 4:
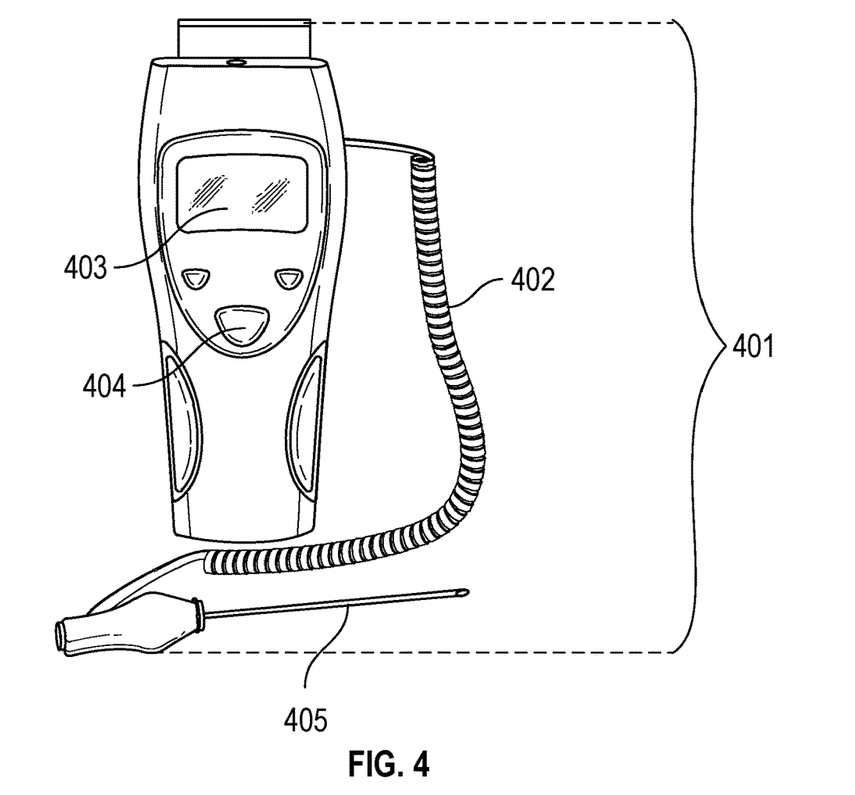
FIG. 4 is a representation of a radiometer according to embodiments.

FIG. 4 is a representation of an example radiometer that is integrated with the phototherapy device. The radiometer 401 has a stretchable cord 402 to allow for needed extension, a digital display 403, user interface elements, such as, for example, buttons 404, and sensor 405. The stretchable cord 402 can be replaced, in embodiments, with a retractable cable, which would also allow for data transfer. In embodiments, the radiometer sensor 405 could wirelessly transmit data to the radiometer 401, such that there is no physical connection between the radiometer sensor 405 and the radiometer 401. If wireless, the radiometer sensor 405 can be stored in the radiometer 401 when not in use. It can also be magnetically attached, or integrated with the light source. A notification can be provided if the wireless radiometer sensor is not returned to the radiometer after a certain time period, or if the wireless radiometer sensor is too far away from the radiometer. The radiometer 401 can be configured to collect data continuously or intermittently. If collection is intermittent, the user can specify the intervals of data collection.

In some embodiments, the radiometer 401 is connected to the phototherapy apparatus, and the radiometer sensor 405 is integrated with the phototherapy apparatus via an extendible or stretchable cord 402. In some embodiments the radiometer is integrated with the phototherapy apparatus via an extendible or stretchable cord. In some embodiments, the radiometer can be built-in or fixed to the phototherapy apparatus. In some embodiments, the radiometer can be miniaturized. The radiometer can measure irradiance of light from different wavelengths of the light spectrum, which can correspond to different colors of light. The radiometer can also measure irradiance from different types of light sources, such as mats, blankets or overhead lights, and can switch between light sources, such as with a toggle switch as described more thoroughly above.

The digital display 403 can display date and time, date and time therapy started, type of therapy (e.g., single, double, or triple), running total of current therapy, start new treatment feature (initial set-up and choose settings/therapy), end of treatment feature (displays the settings/therapy used, start date/time through end date/time and total hours/length of treatment), re-set feature to clear settings and put unit away or begin new therapy/treatment, light intensity/irradiance readings, the wavelength range of the light, total microwatts delivered, microwatts delivered for different wavelength ranges. running total of current therapy times for different wavelength ranges, total number of hours product has been in use, for example using a sensor within or under the light tray (to track the life of the lights and how many hours are left before the lights need replacement per manufacturer recommendations), and/or date last calibrated (to track and maintain equipment per manufacturer recommendations). In embodiments, all components will be capable of being removed, reset, calibrated, and serviced independently of one another.

While the display is illustrated as integrated with the radiometer, the skilled artisan will appreciate that the display can be separate from the radiometer while remaining a component of the phototherapy apparatus. In some embodiments, the radiometer has a memory system and a display system that will be able to display the last few light irradiance readings, light wavelength ranges, total microwatts delivered, microwatts delivered for different wavelength ranges, date and time, the total number of hours the product has been in use (to track the life of the lights and how many hours are left before the lights need replacement per manufacturer recommendations), and/or the total number of hours the product has been in use per patient/treatment (to track length/hours of treatment used). The radiometer can also measure and display readings from other light sources or phototherapy equipment, and can keep track of the equipment and data associated with individual patients. In some embodiments, the radiometer will function similar the odometer of a car where it will keep track of your total mileage on your car as well as miles per "trip"—the radiometer will keep track of total hours the product has been in use per patient as well as hours per treatment.

In some embodiments, the radiometer has user interface elements, such as, for example, buttons 404, capacitive touch sensors, switches, touchscreen controls, and/or a communications interface for receiving user input from a personal mobile device, another electronic device, and/or a separate control panel. In some embodiments, the radiometer has three user interface elements. For example, in some embodiments, a button can be pressed to reset the display for the number of hours per treatment, for example, for the initiation of a new treatment. This is similar to the odometer analogy of pressing a button to start the mileage at zero to measure the distance of a particular trip so that the total miles it takes for that trip will be known at the completion of the trip, and the button can be pressed again to reset it back to zero and start a new trip. In some embodiments, a button can be pressed to reset the display for the number of hours per patient, for example for the initiation of a new patient. The interactive user interface will also allow a user to view all current and past settings on demand.

In some embodiments one or more buttons change the settings of the radiometer and/or the light source. In some embodiments the buttons cause the display to show different types of data. In some embodiments the buttons cause the retrieval of different types of data.

In some embodiments, the phototherapy apparatus has a potentiometer. Through the push of a button, one can adjust the light intensity/irradiance to increase light intensity, decrease light intensity, or have it set for the standard manufacturer setting. This potentiometer can be analogous to a light dimmer switch in a house that allows one to achieve the exact amount of light desired, and it can be fully automated or manual.

In some embodiments, the radiometer can have a blinking "low" notification, when light irradiance is measured, if the optimal light irradiance is not being achieved (for example, less than 30 microwatts/cm$^2$). This notification can allow for the appropriate intervention, for example, adjusting the light to be closer to the patient, increasing the potentiometer to deliver more intensity/irradiance, or having the unit inspected by clinical engineering.

In some embodiments, the radiometer can have a backup battery system. In some embodiments, the radiometer can have an electrical connection or prongs to connect directly with the phototherapy light or to the associated control unit. The connection can be through any means, such as USB, Bluetooth, or electrical cable, to name a few examples.

Figure 5:
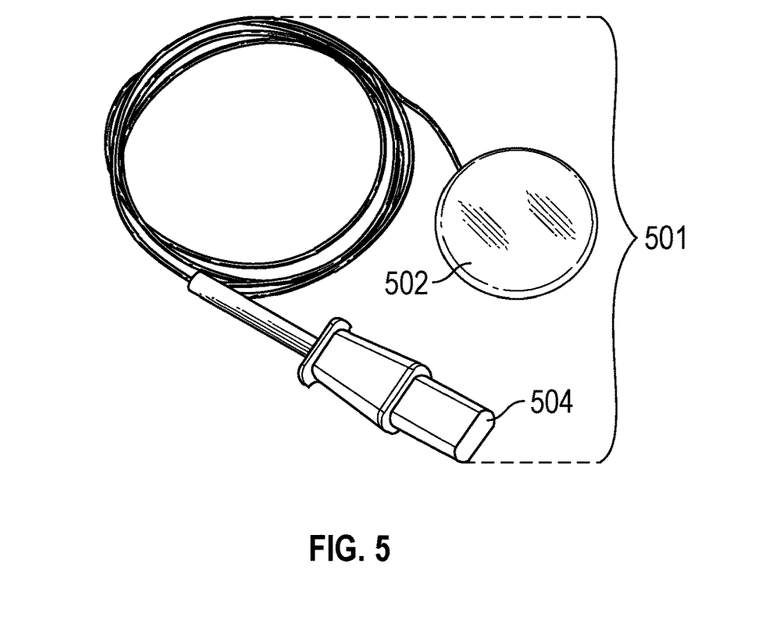
FIG. 5 is a representation of a transcutaneous bilirubin reader according to embodiments.

FIG. 5 shows a transcutaneous bilirubin reader 501 with a sensor/probe 502, according to some embodiments. In some embodiments the skin around the sensor/probe 502, and in some cases the probe itself, is covered by a light opaque adhesive covering 503 (shown in FIG. 6), such as an appropriate sticker, to protect the area of skin from receiving light. The transcutaneous bilirubin reader can detect current bilirubin level, temperature, and the distance between the patient and the light source. In some embodiments, the transcutaneous bilirubin reader is integrated with a sensor that can detect distance from the bili light. In embodiments, the sensor/probe 502 is placed on a patient in a location that receives a minimal amount of direct light from the light source. The location can include the patient's side or an area near the patient's armpit. In embodiments, the sensor/probe 502 is attached to the patient's skin via an adhesive, such as an opaque sticker. An opaque sticker or other opaque covering 503 over the sensor/probe 502 and surrounding skin prevents light from reaching the area of the skin from which the sensor/probe 502 draws readings. That way, the sensor/probe 502 can read bilirubin levels from the patient's non-exposed skin. The opaque sticker can be removed and replaced as needed with the light turned off, though the underlying probe does not necessarily need to be replaced. In embodiments, a plug 504 on the transcutaneous bilirubin sensor 501 can be used to integrate the transcutaneous bilirubin sensor with the phototherapy apparatus.

Figure 7:
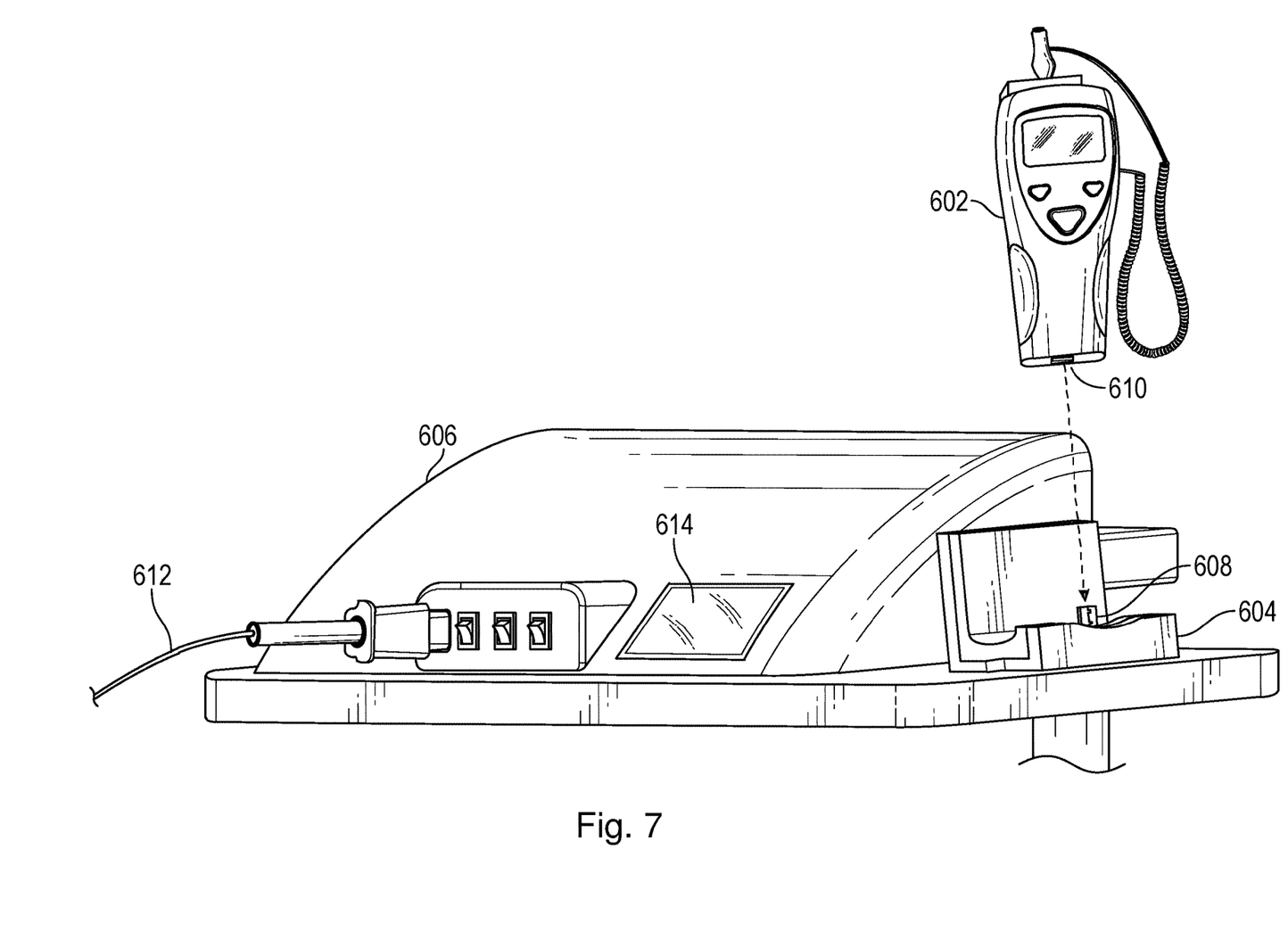
FIG. 7 is a representation of a radiometer entering a docking station of a phototherapy apparatus according to embodiments.

FIG. 7 illustrates the integration of a radiometer 602 with a phototherapy apparatus 606. In embodiments, the phototherapy apparatus 606 includes a docking station 604 to receiver the radiometer 602. In embodiments, the docking station 604 is configured to hold the radiometer 602 with a "cup and cup holder" fit. In embodiments, the docking station 604 and radiometer 602 can include one or more connections to hold the radiometer 602 in place. For example, the docking station 604 can hold the radiometer 602 such that in the absence of connections, the radiometer 602 would fall. For instance, the connections can comprise corresponding magnets that hold a surface of the radiometer 602 against a surface of the docking station 604. In embodiments, the connections, such as magnets, can be used along with the cup holder embodiment, such that the connections reinforce the position of the radiometer 602 in the docking station 604. In embodiments, the one or more connections can include a universal serial bus (USB) connection. Likewise, the transcutaneous bilirubin reader 612 can be connected to the phototherapy apparatus 606 through any number of means, including for example those means discussed with respect to the connection between the radiometer 602 and the phototherapy apparatus 606.

For example, FIG. 7 illustrates an embodiment in which the docking station 604 includes a USB plug 608 and the radiometer 602 includes a USB receptacle 610. The radiometer 602 can be placed into the docking station 604 such that the USB receptacle 610 on the radiometer 602 receives the USB plug 608 in the docking station 604. The USB connection can allow for power and data transfer between the phototherapy apparatus 606 and its control unit or system and the radiometer 602, which can allow for data from all sources to be uploaded to the electronic healthcare records system. For instance, the radiometer 602 can be charged via the USB connection and also relay irradiance data to the control system of the phototherapy apparatus 606.

Other connections can be used to achieve these tasks in various embodiments. For example, other standard electrical connectors can be used for power or data transfer or custom connectors can be implemented. In embodiments, wireless charging can be achieved when the radiometer 602 is placed in the docking station 604. Likewise, data can be wirelessly transmitted from the radiometer 602. Mechanical connectors can be used in various embodiments. For example, the docking station 604 can comprise a bracket that holds the radiometer 602 in place.

In some embodiments, the phototherapy apparatus has a memory chip/system for storing values in logical memory addresses. Stored values can include patient data, phototherapy prescription information, current bilirubin level, target bilirubin level, bili light intensity level, current irradiance, target irradiance, other values relevant to phototherapy treatment, and/or a combination of values. In embodiments, the phototherapy apparatus 606 can include a dedicated display 614 for displaying these and other values. The dedicated display 614 can further allow for user input to control the phototherapy apparatus 606 and/or its various components.

In some embodiments, the apparatus has a control system. The control system can be built into the light source housing or can be positioned separately, for instance in a separate computing device. The control system can be configured with automatic features. Upon initiation of phototherapy, the user can input data such as distance of patient from light, intensity level, irradiance level, light spectrum wavelengths, total microwatts delivered, microwatts delivered for different wavelength ranges, and/or desired bilirubin levels to be achieved (based, for example, on gestational age and/or physician orders).

In some embodiments, the control system is configured to utilize a feedback system with the radiometer and/or transcutaneous bilirubin reader. The radiometer and/or transcutaneous bilirubin reader (including the bilirubin sensor and the sensor that can detect distance from the bili light) can send data regarding irradiance, bilirubin levels, and/or distance the patient is away from the light to the control system. The control system can automatically initiate a signal and/or notification and specify "check distance" on a display screen if the distance from patient has changed from the desired/set distance that was input (for example, if a component of the apparatus gets knocked out of place, etc.). If the light irradiance reaching the patient falls below a desired number, the control system can automatically adjust the potentiometer to increase the light intensity/irradiance to the necessary level to achieve the desired number. The control system can accept an input of a desired range for the irradiance (for example, 30-50 microwatts/cm$^2$), and the control system can decrease the potentiometer to function within the desired range.

In some embodiments, the control system can, based on feedback from the feedback system, send a "therapy completed" signal and/or notification once the desired/set bilirubin levels and/or phototherapy treatment time are achieved. Such a feature can prevent unnecessary treatment time. In some embodiments, the control system can automatically shut off the phototherapy lights and/or the apparatus. For example, when the "therapy completed" notification is triggered, the lights will shut off (and the shut-off time can be stored) but the "therapy completed" notification will continue until addressed by the healthcare provider or nurse. In some embodiments, the automatic shut off is an option that can be selected. For example, there can be orders from a physician to select the automatic shut-off option and additional orders for the healthcare provider or nurse to draw any follow-up lab work.

Any one of these features of a control system (e.g., notification or automatic adjustment), can be implemented alone, manually, or in combination.

In some embodiments, the apparatus can be fully automated and programmed/formatted to any electronic healthcare records software, whether via cable/cord, remote or wireless/bluetooth connection. From this, data can be automatically "pulled in" directly to the patients charting/documentation. That is, all gathered data can be aggregated and compiled for use with any electronic healthcare records software. Such data can include the unit number used, therapy used/settings, duration (start/stop times as well as total running therapy time), light intensity readings, etc. In embodiments, the phototherapy apparatus can be in communication with a scanner, for example via the electronic healthcare records system. The scanner can scan a patient's wristband or chart to retrieve data associated with the patient, and the scanner can scan the phototherapy unit and associated equipment to upload data from these sources as well. This can associate, for example, a particular light source with a particular patient. In embodiments, this data can be used by the control system of the phototherapy apparatus to automatically set up an initial treatment regimen. In embodiments, the pairings of particular phototherapy apparatuses with particular patients can be logged, such that a returning patient can be matched to the same phototherapy apparatus previously used, which may be helpful given possible variations between pieces of equipment.

In some embodiments, the apparatus has a timer. The timer can detect and keep track (e.g., date/time/duration) of every time the phototherapy lights are turned off during treatment (to let the parent hold or feed infant, to change protective eyewear, to start IV, etc.) and then resumed, and automatically pulls that data into documentation/charting, where a nurse can then document comments. The control system can automatically subtract these "off" times from the running total of the treatment time so that a "true number" of how long the lights have actually been on the patient is tracked.

In some embodiments, all components (including the phototherapy light, unit, radiometer, bilirubin reader, and/or timer) can be removed, reset, calibrated and serviced independently. In some embodiments, each phototherapy unit has a unit number assigned to all components.

In general, the word "module," as used herein, is used in its broad and ordinary sense and refers, for example, to logic embodied in hardware or firmware, or to a collection of software instructions, possibly having entry and exit points, written in a programming language, such as, for example, Java, C or C++. A software module may be compiled and linked into an executable program, installed in a dynamic link library, or may be written in an interpreted programming language such as, for example, BASIC, Perl, or Python. It will be appreciated that software modules may be callable from other modules or from themselves, and/or may be invoked in response to detected events or interrupts. Software instructions may be embedded in firmware, such as an EPROM. It will be further appreciated that hardware modules may be comprised of connected logic units, such as gates and flip-flops, and/or may be comprised of programmable units, such as programmable gate arrays, application-specific circuits, or hardware processors. The modules described herein are preferably implemented as software modules, but may be represented in hardware or firmware. Generally, the modules described herein refer to logical modules that may be combined with other modules or divided into sub-modules despite their physical organization or storage.

The various illustrative logical blocks, modules, data structures, algorithms, equations, and processes described herein may be implemented as electronic hardware, computer software, or combinations of both. To clearly illustrate this interchangeability of hardware and software, various illustrative components, blocks, modules, and states have been described above generally in terms of their functionality. However, while the various modules are illustrated separately, they may share some or all of the same underlying logic or code. Certain of the logical blocks, modules, and processes described herein may instead be implemented monolithically.

The various illustrative logical blocks, modules, data structures, and processes described herein may be implemented or performed by a machine, such as a computer, a processor, a digital signal processor (DSP), an application specific integrated circuit (ASIC), a filed programmable gate array (FPGA) or other programmable logic device, discrete gate or transistor logic, discrete hardware components, or any combination thereof designed to perform the functions described herein. A processor may be a microprocessor, a controller, a microcontroller, a state machine, combinations of the same, or the like. A processor may also be implemented as a combination of computing devices—for example, a combination of a DSP and a microprocessor, a plurality of microprocessors or processor cores, one or more graphics or stream processors, one or more microprocessors in conjunction with a DSP, or any other such configuration.

The blocks or states of the processes described herein may be embodied directly in hardware or firmware, in a software module executed by a hardware processor, or in a combination of the two. For example, each of the processes described above may also be embodied in, and fully automated by, software modules executed by one or more machines such as computers or computer processors. A module may reside in a non-transitory computer-readable storage medium such as RAM memory, flash memory, ROM memory, EPROM memory, EEPROM memory, registers, a hard disk, a removable disk, an optical storage disk, memory capable of storing firmware, or any other form of computer-readable storage medium. An exemplary computer-readable storage medium can be coupled to a processor such that the processor can read information from, and write information to, the computer readable storage medium. In the alternative, the computer-readable storage medium may be integral to the processor. The processor and the computer-readable storage medium may reside in an ASIC. Hardware components may communicate with other components via wired or wireless communication networks such as, e.g., the Internet, a wide area network, a local area network, or some other type of network.

Depending on the embodiment, certain acts, events, or functions of any of the processes or algorithms described herein can be performed in a different sequence, may be added, merged, or left out altogether. Thus, in certain embodiments, not all described acts or events are necessary for the practice of the processes. Moreover, in certain embodiments, acts or events may be performed concurrently, e.g., through multi-threaded processing, interrupt processing, or via multiple processors or processor cores, rather than sequentially.

Conditional language used herein, such as, among others, "can," "could," "might," "may," "e.g.," and the like, unless specifically stated otherwise, or otherwise understood within the context as used, is intended in its ordinary sense and is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without author input or prompting, whether these features, elements and/or steps are included or are to be performed in any particular embodiment. The terms "comprising," "including," "having," and the like are synonymous, are used in their ordinary sense, and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Conjunctive language such as the phrase "at least one of X, Y and Z," unless specifically stated otherwise, is understood with the context as used in general to convey that an item, term, element, etc. may be either X, Y or Z. Thus, such conjunctive language is not generally intended to imply that certain embodiments require at least one of X, at least one of Y and at least one of Z to each be present.

It should be appreciated that in the above description of embodiments, various features are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that any claim require more features than are expressly recited in that claim. Moreover, any components, features, or steps illustrated and/or described in a particular embodiment herein can be applied to or used with any other embodiment(s). Further, no component, feature, step, or group of components, features, or steps are necessary or indispensable for each embodiment. Thus, it is intended that the scope of the inventions herein disclosed and claimed below should not be limited by the particular embodiments described above, but should be determined only by a fair reading of the claims that follow.

What is claimed is:

1. A bilirubin reader for use in a phototherapy system to monitor bilirubin levels in a patient, the system comprising:

a transcutaneous bilirubin sensor for placement adjacent skin of a patient, the transcutaneous bilirubin sensor being positioned to measure one or more parameters in the patient when placed adjacent the skin of the patient; and a substantially opaque covering configured to attach to the skin of the patient and cover the transcutaneous bilirubin sensor to reduce exposure of the transcutaneous bilirubin sensor to light.

2. The bilirubin reader of claim 1, wherein the transcutaneous bilirubin sensor monitors the one or more patient parameters continuously and transmits data associated with the one or more patient parameters to a processor for processing the data associated with the patient parameters as measured by the transcutaneous bilirubin sensor.

3. The bilirubin reader of claim 1, wherein the transcutaneous bilirubin sensor monitors the one or more patient parameters intermittently and transmits data associated with the one or more patient parameters to a processor for processing the data associated with the patient parameters as measured by the transcutaneous bilirubin sensor.

4. The bilirubin reader of claim 3, wherein the transcutaneous bilirubin sensor monitors the one or more parameters hourly.

5. The bilirubin reader of claim 1, wherein the one or more parameters is selected from a group consisting of bilirubin levels, temperature, and irradiance.

6. The bilirubin reader of claim 1, wherein the transcutaneous bilirubin sensor identifies and transmits data associated with a distance between the patient and a light source.

7. The bilirubin reader of claim 2, wherein the transcutaneous bilirubin sensor transmits data to the processor wirelessly.

8. The bilirubin reader of claim 1, wherein the opaque covering comprises an adhesive so as to attach the covering to the skin of the patient to maintain the position of the transcutaneous bilirubin sensor relative to the patient.

9. The bilirubin reader of claim 1, wherein the opaque covering is configured to prevent light from reaching an area of the skin adjacent the transcutaneous bilirubin sensor so that the transcutaneous bilirubin sensor may draw readings from non-exposed skin.

10. A method of monitoring a patient using a phototherapy system, the method comprising the steps of:
a) attaching a transcutaneous bilirubin sensor to the patient to monitor one or more parameters of the patient;
b) covering the transcutaneous bilirubin sensor with a substantially opaque covering to reduce exposure of the transcutaneous bilirubin sensor to a bilirubin light source when being used in association with the phototherapy system;
c) attaching the substantially opaque covering to skin of the patient;
d) collecting data associated with the one or more parameters of the patient; and
e) transmitting collected data from the transcutaneous bilirubin sensor to a processor for processing data associated with the patient parameters as measured by the sensor.

11. The method of claim 10, wherein step b) further comprises using an adhesive to attach the substantially opaque covering to the patient to help maintain the position of the transcutaneous bilirubin sensor relative to the patient.

12. The method of claim 10, wherein the one or more parameters of the patient include one or more of bilirubin levels, temperature, or irradiance.

13. The method of claim 10, wherein step e) comprises transmitting the data to the processor wirelessly.

14. The method of claim 10, further comprising positioning the substantially opaque covering to prevent light from reaching an area of the skin adjacent the transcutaneous bilirubin sensor so that the transcutaneous bilirubin sensor may draw readings from non-exposed skin.

15. An integrated phototherapy system comprising:
a light source to transmit light to a patient;
a processor to receive data associated with predetermined patient parameters;
a transcutaneous bilirubin sensor for placement adjacent skin of the patient to collect data associated with the predetermined patient parameters and transmit the data to the processor; and
a substantially opaque covering configured to attach to the skin of the patient and cover the transcutaneous bilirubin sensor to reduce exposure of the transcutaneous bilirubin sensor to light.

16. The system of claim 15, wherein the transcutaneous bilirubin sensor collects and transmits the data to the processor for processing the data associated with the patient parameters as measured by the transcutaneous bilirubin sensor.

17. The system of claim 15, wherein the substantially opaque covering is configured to prevent light from reaching an area of the skin adjacent the transcutaneous bilirubin sensor so that the transcutaneous bilirubin sensor may draw readings from non-exposed skin.

18. The system of claim 15, wherein the transcutaneous bilirubin sensor transmits the data to the processor wirelessly.

19. The bilirubin reader of claim 1, wherein the light is a bilirubin light associated with the phototherapy system.

20. The integrated phototherapy system of claim 15, wherein the light is a bilirubin light associated with the phototherapy system.

21. The bilirubin reader of claim 1, wherein the processor is programmed to perform at least one of displaying the data, transmitting the data to a healthcare records system, controlling one or more functions of the phototherapy system, generating notifications, receiving user input, or storing the data via a memory device.

22. The integrated phototherapy system of claim 15, wherein the processor is programmed to perform at least one of displaying the data, transmitting the data to a healthcare records system, controlling one or more functions of the phototherapy system, generating notifications, receiving user input, or storing the data via a memory device.

23. The method of claim 10, wherein the processor is programmed to perform at least one of displaying the data, transmitting the data to a healthcare records system, controlling one or more functions of the phototherapy system, generating notifications, receiving user input, or storing the data via a memory device.

24. The integrated phototherapy system of claim 22, wherein controlling one or more functions of the phototherapy system comprises adjusting a light intensity, adjusting a position of the light relative to the patient, starting operation of the phototherapy system, or stopping operation of the phototherapy system.

* * * * *